United States Patent [19]

Kepley

[11] Patent Number: 5,038,756
[45] Date of Patent: Aug. 13, 1991

[54] NEEDLE INTERFACE BOOT FOR ULTRASONIC SURGICAL INSTRUMENT

[75] Inventor: Kevin P. Kepley, St. Louis, Mo.

[73] Assignee: Storz Instrument Company, St. Louis, Mo.

[21] Appl. No.: 428,523

[22] Filed: Oct. 30, 1989

[51] Int. Cl.5 ............................................. A61B 17/00
[52] U.S. Cl. ................................... 128/24 AA; 604/22
[58] Field of Search ...................... 128/24 AA; 604/22

[56] References Cited

U.S. PATENT DOCUMENTS

| | | | |
|---|---|---|---|
| 3,805,787 | 4/1974 | Banko | 128/24 AA |
| 4,681,561 | 7/1987 | Hood et al. | 604/22 |
| 4,816,017 | 3/1989 | Hood et al. | 604/22 |
| 4,816,018 | 3/1989 | Parisi | 128/24 AA |
| 4,867,141 | 9/1989 | Nakada et al. | 128/24 AA |
| 4,886,060 | 12/1989 | Wiksell | 128/24 AA |

Primary Examiner—Lee S. Cohen
Assistant Examiner—John D. Zele
Attorney, Agent, or Firm—David A. Warmbold

[57] ABSTRACT

A needle interface boot for use in an ultrasonic ophthalmic surgical instrument of the type incorporating coaxial irrigation and aspiration functions which comprises a conically-shaped hollow instrument. The boot is made from a compliant silicone or plastic-type material and is positioned within the irrigation channel surrounding the interface or connection between the vibratory transmissive member or resonator and the needle probe to prevent irrigation fluid from contacting the flat projecting surfaces of this interface and, thus, reduces objectionable cavitation and bubble formation within the irrigation fluid to be delivered to the operative site during use of such a surgical instrument.

4 Claims, 2 Drawing Sheets

NEEDLE INTERFACE BOOT FOR ULTRASONIC SURGICAL INSTRUMENT

FIELD OF THE INVENTION

The present invention relates generally to fluid-irrigated, ultrasonically-operated cutting instruments, and particularly to surgical instruments of the type which employ ultrasonic energy for the emulsification of tissue. This invention especially relates to an ultrasonic needle interface boot surrounding the connection or interface between the transducer and needle probe to improve the operating characteristics of an ultrasonic surgical irrigation-aspiration instrument, such as is used in eye surgery.

BACKGROUND OF THE INVENTION

It is now commonly accepted that the vision impairment disease known as cataracts can be alleviated by surgically replacing the natural lens of the eye with an artificial intraocular lens. The condition of cataracts is characterized by the clouding of the natural lens of the eye so that the amount of light which reaches the retina is substantially reduced or completely eliminated.

Surgical instruments utilizing ultrasonic vibrations in combination with the circulation of irrigation liquid over the operative site for the removal of tissue from a biological body are well-known and widely used, particularly in enclosed and substantially enclosed operative sites. Such surgical instruments are particularly well adapted for the removal of cataracts and other surgical procedures performed on the eye. Ultrasonic surgical instruments of the type with which the present invention is primarily concerned employ an elongated probe or hollow needle having an end threadedly attached through a vibration transmissive member or resonator to a transducer for supplying ultrasonic energy to the other or free end of the hollow needle. The ultrasonic energy is emitted to dislodge and breakup or emulsify tissue from the operative site for removal by aspiration. Irrigating fluid is delivered through the instrument into a shield, or sheath, surrounding the body of the needle for discharge adjacent to the tip or free end of the needle and is returned by suction through a hollow center in the tubular body of the needle.

An ultrasonic surgical aspirator of this type is shown in U.S. Pat. No. 3,805,787 as including conduits for applying suction through the center of the ultrasonically operative needle and for supplying irrigating fluid around the outer surface of the needle through a passage defined by a tubular shield. The irrigation fluid flows around the free end of the needle element and back through the center of the hollow needle to effectively irrigate and remove the discharged and emulsified tissue. Another such ultrasonic surgical aspirator is manufactured and sold by Storz Instrument Company, Model No. D-8110, located in St. Louis, Miss.

Significant attention in the art for improving the operative characteristics of these instruments for the convenience of the surgeon and to enhance the efficacy of the instrument for the safety of the patient has been directed to solving a number of problems. For example, it has been desired to utilize greater electrical power and circuitry to energize the transducer contained within the ultrasonic surgical instrument to obtain greater excursion or vibratory action of the needle probe. However, such increased power and vibratory action can create cavitation bubbles caused by the ultrasonically-vibrating member and as a result of directing the irrigating fluid past the vibrating connection or interface between the resonator and needle probe. The needle probes used in these instruments are generally standardized in the industry and typically include a standardized threaded portion at one end for attachment to the resonator or vibration transmissive member and a square shank portion immediately adjacent said threads for receiving a tool for securely attaching the needle probe to the ultrasonic instrument. It is believed that the cavitation bubbles are created in part by the ultrasonic energy being radiated into the irrigation fluid via the sharp angles of the resonator member and needle probe connection or interface site. These cavitation bubbles create a visual obstruction in delicate surgery, and an annoyance in the eye during surgery. Usually the surgeon is required to interrupt the surgery to permit the aspiration system to remove the bubbles before resuming the surgery.

One method of attempting to reduce cavitation bubbles in such an ultrasonic surgical instrument is shown in U. S. Pat. Nos. 4,681,561 and 4,816,017, both entitled "Ultrasonic Decoupling Sleeve". The decoupling sleeve attempts to define a new flow path within the irrigation fluid path existing within the ultrasonic surgical instrument. However, such a decoupling sleeve has been found to be ineffective in reducing cavitation bubbles occurring within such instruments.

Accordingly, it is desired to isolate the resonator/needle probe interface from the irrigation fluid present in the fluid path between the resonator/needle probe structures and the outer shield to avoid cavitation bubbles in the irrigation fluid path of the ultrasonic instrument.

OBJECTS OF THE INVENTION

It is an object of the present invention to improve an ultrasonic surgical instrument of the type described by reducing or eliminating cavitation and bubble formation in the irrigation fluid.

It is a further object of the present invention to provide a Needle Interface Boot (NIB) for an ultrasonic surgical instrument of the type described which reduces or eliminates cavitation and bubble formation with the irrigation fluid.

It is a further object of the invention to provide an improved ultrasonic surgical instrument which avoids the deficiencies of the prior art devices discussed above, and which enables a more efficient, effective and safe use of the instrument for a surgical cataract procedure.

SUMMARY OF THE INVENTION

In accordance with the present invention, an improved ultrasonic surgical instrument is provided of the type having an elongated, generally cylindrical handpiece containing a transducer and vibratory transmissive member or resonator adapted to receive a hollow needle or probe on its free end, an elongated tubular aspiration fluid conduit for sunctioning fluids through the hollow needle and handpiece, and an irrigation fluid supply conduit for supplying an irrigation fluid to the operative tip of the needle probe. The improvement according to the present invention comprises a component for use in such combination which comprises a generally conically-shaped Needle Interface Boot (NIB) made from a compliant silicone or plastic type material for surrounding the interface or connection between the needle probe and resonator. During operation of the instrument, the interface portion oscillates axially back and forth along the central longitudinal axis of the resonator and needle probe. It is believed that the rapid movement of flat areas of the needle probe and, to a lesser extent, the rounded horn portion of the needle probe, causes a cavitation to occur in the irrigation fluid chamber. This cavitation produces air bubbles which can be carried by the irrigation fluid into the eye. The boot surrounds and isolates the interface areas of the resonator and needle probe from the irrigation fluid to dramatically decrease the quantity of air bubbles produced during operation of the ultrasonic surgical instrument.

Preferably, the needle interface boot comprises a conically-shaped cylinder having a wall thickness which is greater at the proximal end or portion that fits over the resonator than the distal end or portion fitting around the longitudinally extending portion of the needle probe. The inside diameter of the boot, in that portion fitting over the resonator, should be slightly less than the outside diameter of the resonator to ensure a good seal therebetween and to assist in holding the boot in place. Furthermore, the inside diameter of the boot, in that portion fitting over the needle probe, should be slightly less than the outside diameter of the straight portion of such needle probe to ensure a good interference fit and seal and to assist in holding the boot in place during operation of the instrument. It is important that irrigation fluid not be allowed to flow into the area between the resonator/needle and boot or, otherwise, cavitation and bubble production will occur.

The outer surface of the interface needle boot presents a smooth, rounded surface to the irrigation fluid to dramatically reduce cavitation in the irrigation fluid chamber and, consequently, the size and quantity of air bubbles produced by operation of this type of ultrasonic surgical instrument.

BRIEF DESCRIPTION OF THE DRAWINGS

Other features and advantages of the invention will be apparent from the detailed description contained hereinbelow, taken in conjunction with the drawings, in which.

The drawings are illustrative of the concept of the invention and should not unduly limit the invention which could include other embodiments obvious to a person of ordinary skill in the art within the spirit of the invention.

DETAILED DESCRIPTION OF THE PREFERRED EMBODIMENT

Figure 1:
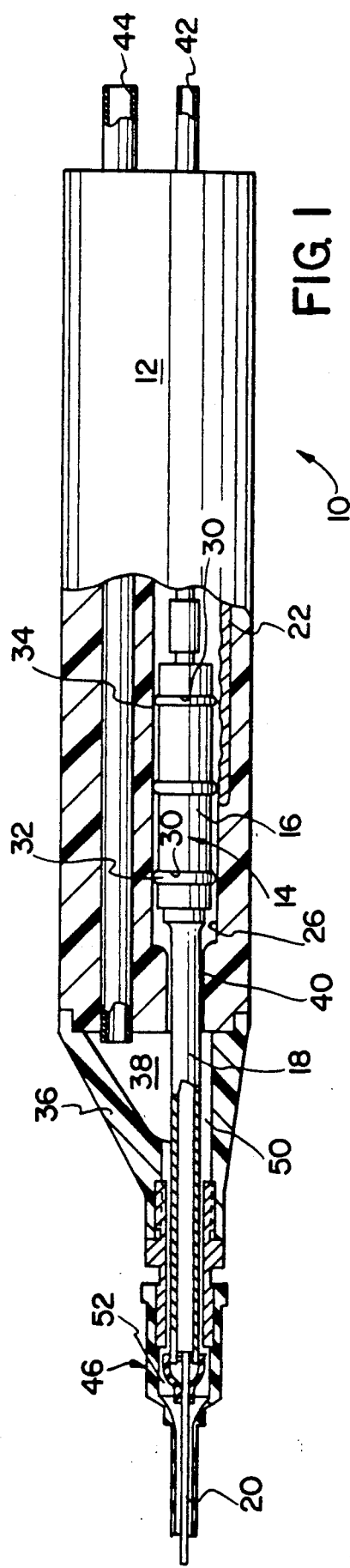
FIG. 1 is a longitudinal sectional view, with portions broken away, of a conventional, ultrasonic surgical instrument of the type utilizing an irrigation sleeve and embodying the present invention.

The conventional ultrasonic ophthalmological surgical instrument which incorporates coaxial irrigation and aspiration functions to which the needle interface boot of the present invention is particularly applicable is designated generally by the reference numeral 10 in FIG. 1. A surgical instrument 10 of this type comprises a handpiece or housing 12 enclosing and supporting a vibratory body 14 including a piezoelectric or magnetostrictive transducer 16 and a vibratory transmissive member or resonator 18 having an ultrasonically-vibrated needle probe 20 mounted on its distal end in an outwardly space relation to the housing. Electrical energy is provided from a suitable high-frequency source through conductors 22 to the transducer 16. The vibrating body assembly is mounted within a cavity 26 of handpiece 12. A pair of radially extending, axially-spaced flanges 30 and a pair or resilient O-ring gasket members 32 and 34 effectively isolate the handpiece 12 from vibrations induced by transducer 16.

An end cap 36 is affixed on an end of handpiece 12 and forms an internal irrigation fluid chamber 38. The resonator 18 extends longitudinally through the fluid chamber 38 and end cap 36. An O-ring seal member 40 provides a fluid seal between handpiece 12 and resonator 18 to prevent the flow of irrigation fluid inside the handpiece. The instrument is provided with an aspiration conduit 42 which is connected to a source of vacuum and an irrigation conduit 44 connected to a source of irrigation fluid. Both conduits 42 and 44 pass longitudinally through the handpiece 12 leading to the region of the end cap 36. A removable sleeve or shield member 46 is mounted on the distal end of end cap 36 and extends in surrounding relation to the elongated needle probe 20. The sleeve member 46, which will be described more fully below herein, provides a coaxial annular passage for supplying irrigation fluid to the surgical site of the distal tip of the needle probe 18.

Figure 2:
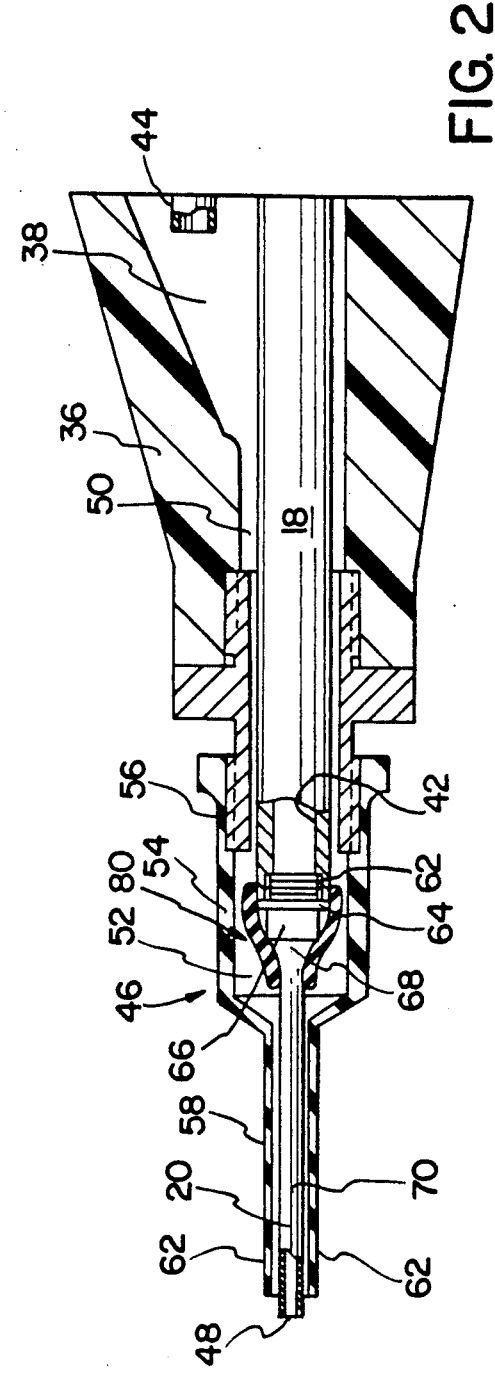
FIG. 2 is an enlarged, longitudinal cross-sectional needle interface boot employed on the instrument shown in FIG. 1.

Referring now to FIG. 2, an enlarged view of the longitudinal cross-section of the end cap 36 at the distal end of the handpiece 12 is shown. An axial bore 48 in the needle probe 20 communicates with the aspiration conduit 42 through conventionally drilled passages in the resonator 18 and the handpiece 12. The region between the resonator 18 and the end cap 36 defines the irrigation fluid chamber 38 and an axially extending conduit 50. The irrigation conduit 44, through the handpiece 12, supplies irrigation fluid into the irrigation chamber 38 and conduit 50. The sleeve member 46 surrounds the ultrasonic needle probe 18 to provide a coaxial irrigation fluid channel 52 which receives irrigation fluid from the axially extending conduit 50 and conveys it to the surgical site.

The sleeve member 46 is hollow and has a body portion 54 which is connected to the end cap 36 through conventional means so as to be in fluid communication with the irrigation supply means in handpiece 12. The body portion 54 of the sleeve member 46 surrounds the interface or connection of the needle probe 20 and the resonator 18 and has an axis which is generally coincident with the axis of the ultrasonically vibrated needle probe 20. Generally, the body portion is cylindrical in shape and includes fastening means at one end of the body portions for connection to the end cap 36. Preferably, mechanical fastening means such as internal threads 56 are provided on the internal wall of the body portion 54 which threadedly engage external threads provided on the end of the end cap 36. The sleeve member 46 also has a radially extending cylindrical portion which defines the axially extending fluid conduit 52 which is sized to fit closely over the external diameter of the needle probe. Side ports 62 are provided in the sleeve member near its distal end to provide free flow of irrigation fluid to the surgical site.

Figure 3:
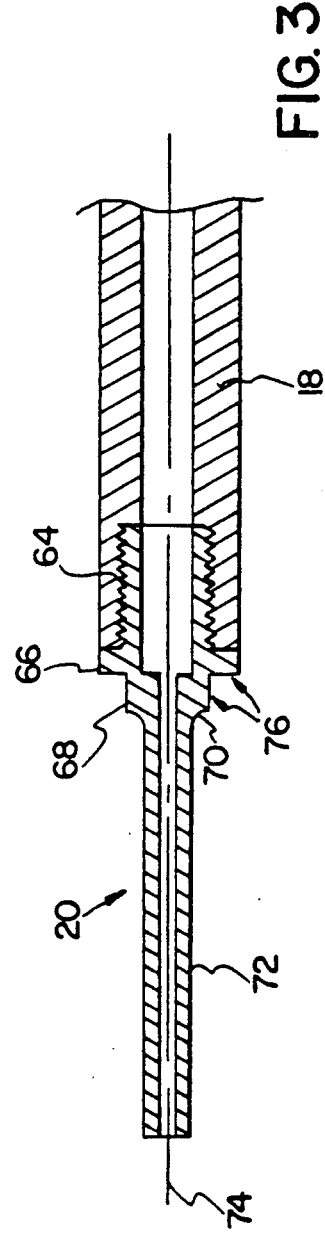
FIG. 3 is an enlarged, cross-sectional view of the interface or connection between the resonator and needle probe showing the details of the needle probe structure.

Referring to FIG. 3, wherein the interface between the resonator 18 and needle probe 20 is shown in greater detail. It can be seen that needle probe 20 has external threads 64 at one end which are received in mating internal threads within the resonator 18. The needle probe 20 has an annular flange 66, a generally square section 68 for receiving a wrench or the like for installing the needle on the resonator, and a needle horn 70 where the configuration of the needle changes from the square section 68 to a smaller circular diameter of the axially extending probe portion 72 of needle probe 20. During operation of the ultrasonic surgical instrument the needle/resonator interface oscillates back and forth, longitudinally along the central axis 74 of the needle probe 20. the movement of the flat areas of the needle probe, designated with arrows at 76, and to a somewhat lesser extent the surface of the needle horn 70 causes cavitation in the irrigation fluid which surrounds the needle and resonator. This cavitation produces air bubbles which can be carried by the irrigation fluid into the eye and obstruct the surgeon's vision during this delicate operation.

The apparatus thus far described is of conventional construction and is commercially available and widely used. The construction and operation of the ultrasonic surgical instrument of the present invention may be substantially identical to that described except for the addition of a needle interface boot of the present invention.

Figure 5:
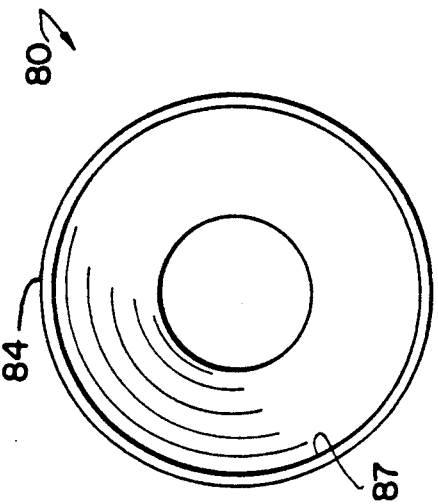
FIG. 5 is an enlarged, elevational view taken on line 5—5 of FIG. 4.
Figure 4:
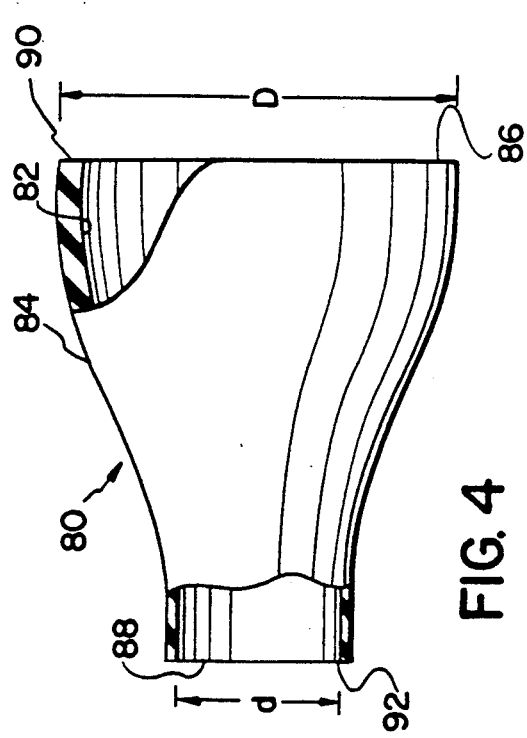
FIG. 4 is an enlarged, elevational view, with portions broken away, of the needle interface boot of the present invention.

Referring now to FIG. 2, which shows the improvements of the present invention wherein a needle interface boot (NIB) 80 is positioned about the interface or connection of the needle probe 20 and resonator 18 and within the body portion 54 of sleeve number 46. The boot 80 is made of a compliant silicone, rubber or plastic material such as neoprene. FIGS. 4 and 5 show the boot 80 to be of generally conical shape having an inner wall 82, outer wall 84, a proximal end 86 and a distal end 88. The wall thickness, designated at 90 of the proximal end 86 of said boot, is greater than the wall thickness designated at 92 of the distal boot end 88. The inside diameter (D) of the proximal end 86 of the boot 80 is sized to be slightly smaller than the external diameter of the end of resonator 18 to ensure a good interference fit to properly secure and seal the boot 80 to resonator 18. The inside diameter (d) of the distal end 88 of boot 80 is sized to be slightly smaller than the outside diameter of the axially extended needle portion 72 to provide a good interference fit to secure and seal the boot 80 to the needle probe 20. It is necessary to have a good seal between the boot 80 and resonator 18 and needle 20 to prevent irrigation fluid from seeping therebetween which would create cavitation and increased bubble formation at the operative site. The outer wall 84 of boot 80 provides a smooth, rounded surface to the irrigation fluid, rather than the flat surfaces 74 and sharp edges of the resonator/needle interface as shown in FIG. 3 such that cavitation and, consequently, bubble formation is eliminated or, at least, greatly reduced during a surgical procedure or during eye surgery.

Furthermore, the beneficial and dramatic results of the use of the present embodiment in an ultrasonic irrigation-aspiration device is described in the following example.

Example 1

A Storz Premiere TM (trademark of Storz Instrument Company) ophthalmic microsurgical instrument utilizing a compatible ultrasonic irrigation-aspiration handpiece with a needle probe (Storz Model No. 1995) was tested with and without the use of a prototype NIB as described in the present invention. The Premiere TM device has a range of power levels such that when low power is supplied to the handpiece a relatively small needle excursion is obtained at the tip portion, and when greater power is supplied to the handpiece a much larger excursion (back and forth longitudinal motion) is obtained at the needle tip.

It was discovered that, without the use of the boot or NIB, bubbles began to form at 20 percent (20%) power delivered to the handpiece. And, at 25 percent (25%) power, bubbles were readily escaping from the tip of the needle. Visibility was noticeably obscured at 30 percent (30%) power such that a surgeon using this device would have difficulty seeing a cataract at the operative site.

However, when the NIB was positioned in the handpiece surrounding the interface between the resonator and needle, the formation of bubbles at the operative site was dramatically reduced. Bubbles did not begin to form until 60 percent (60%) power was delivered to the handpiece, and at 100 percent (100%) power the cavitation and bubble formation was still within an acceptable range such that a surgeon's vision of the operative site would not be unduly obscured.

This invention may be embodied in other specific forms without departing from the spirit or essential characteristics. The present embodiment is, therefore, to be considered in all respects as illustrative and not restrictive, the scope of the invention being indicated by the claims rather than the, foregoing description, and all changes which come within the meaning and range of the equivalents of the claims we therefore intended to be embraced therein.

We claim:

1. In a surgical instrument having an ultrasonically actuated surgical needle, a means for ultrasonically vibrating the needle connected to said needle, and a sleeve member surrounding the connection of the vibrating means and needle and extending about portions of the needle providing a fluid conduit means about said needle and vibrating means for flowing irrigation fluid to a surgical site, the improvement comprising:

needle interface boot means located in said fluid conduit means and surrounding the connection between the needle and vibrating means for sealing said connection of said needle and vibrating means from the irrigation fluid flowing in said fluid conduit means to prevent cavitation and bubble formation within the irrigation fluid.

2. The surgical instrument of claim 1, wherein said vibrating means is an electrically excited transducer and a longitudinally extending resonator attached to said transducer, the resonator having means for securely receiving said needle, and said needle having a generally square portion at a proximal end for assisting in securement of said needle to said resonator and an axially extending needle probe portion having a reduced diameter relative to the width of said square needle portion for insertion into a patient's eye during a surgical operation.

3. The surgical instrument of claim 2, wherein the needle interface boot means comprises a conically shaped cylindrical member having a relatively smooth exterior wall surface, a proximal end having an internal diameter smaller than the external diameter of said resonator, and a distal end having an internal diameter smaller than the external diameter of said axially extending needle probe portion such that, upon insertion of said boot means about the connection between said resonator and needle, a fluid seal is obtained therebetween to prevent the irrigation fluid from contacting the resonator and needle interface to reduce cavitation and bubble formation in the fluid conduit.

4. The surgical instrument of claim 3, wherein the needle interface boot means further includes a varied wall thickness, the wall thickness being greater at the proximal end than at the distal end of said boot, the thicker wall portion of said proximal end being received about the resonator to ensure a secure fit thereto and the thinner wall portion of said distal end being received about the axially extending needle portion to provide a seal therebetween to prevent irrigation fluid from entering the internal area between said boot means and the interface between said resonator and needle.

* * * * *